United States Patent

Gray et al.

Patent Number: 5,098,916
Date of Patent: Mar. 24, 1992

[54] PROPANOBICYCLIC AMINE DERIVATIVES FOR CNS DISORDERS

[75] Inventors: Nancy M. Gray, Ellisville; Brian K. Cheng, St. Charles, both of Mo.

[73] Assignee: G. D. Searle & Co., Chicago, Ill.

[21] Appl. No.: 501,216

[22] Filed: Mar. 29, 1990

[51] Int. Cl.$^5$ .................. A61H 31/445; C07D 211/14
[52] U.S. Cl. .................... 514/325; 514/183;
514/212; 514/424; 514/425; 514/426; 540/451;
540/463; 540/482; 540/485; 540/526; 540/527;
546/203; 546/204; 548/528; 544/380
[58] Field of Search ............... 546/203, 204; 514/325,
514/212, 183, 424, 425, 426; 548/528; 540/451,
463, 482, 485, 526, 527

[56] References Cited

U.S. PATENT DOCUMENTS 3,821,249 6/1974 Malen et al. .................. 540/549
4,758,577 7/1988 Young ........................ 546/204

FOREIGN PATENT DOCUMENTS 1176173 1/1970 United Kingdom .

OTHER PUBLICATIONS

A. F. Gilman et al., *The Pharmacological Basis of Therapeutic* 7th Edn., p. 403, MacMillan (1985).
S. M. Rothman et al., *Annals of Neurology*, 19(2), 105-111 (1986).
C. Carter et al., *J. Pharm. Exp. Ther.*, 247(3), 1222-1232 (1988).

Primary Examiner—C. Warren Ivy
Assistant Examiner—James H. Turnipseed
Attorney, Agent, or Firm—J. Timothy Keane; Paul D. Matukaitis

[57] ABSTRACT

Certain propanobicyclic amine compounds are described for treatment of CNS disorders such as psychotic disorders, convulsions, dystonia and cerebral ischemia. Compounds of particular interest are of the formula

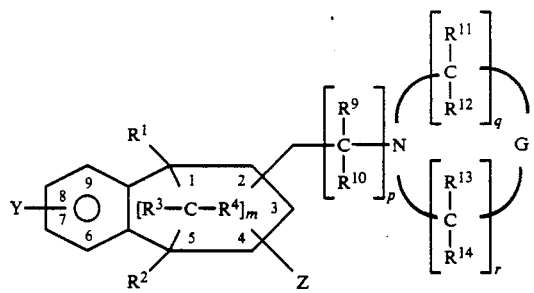

wherein each $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo;
wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, henalkyl and phenyl; wherein G within the nitrogen-containing cyclohetero moiety is selected from

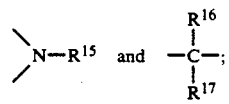

wherein $R^{15}$ is selected from hydrido, alkyl, cycloalkyl, cycloalkylalkyl, phenyl, phenalkyl, alkoxyalkyl and hydroxyalkyl; wherein each of $R^{16}$ and $R^{17}$ is independently selected from hydrido, hydroxy, alkyl, phenalkyl, phenyl, alkoxy, fluoroalkyl and fluoro; wherein m is one or two; wherein p is a number selected from zero through four, inclusive; wherein each of q and r is a number independently selected from one through three, inclusive, with the proviso that sum of q and r is a number from three through six, inclusive; with the further proviso that the nitrogen-containing cyclohetero moiety must be attached at one position selected from $R^3$, $R^4$, ring-position two, ring-position three and ring-position four; or the pharmaceutically-acceptable salts thereof.

22 Claims, No Drawings

PROPANOBICYCLIC AMINE DERIVATIVES FOR CNS DISORDERS

FIELD OF THE INVENTION

This invention is in the field of clinical neurology and relates to a class of compounds, compositions and methods useful for treatment of Central Nervous System (CNS) dysfunctions. Of particular interest is a class of propanobicyclic amine derivatives useful as antipsychotics, as anticonvulsives, as antiischemic agents and to treat dystonic disorders.

BACKGROUND OF THE INVENTION

There are many classes of compounds known for treatment of psychotic disorders. For example, current therapeutic treatments for psychoses use compounds classifiable as tricyclic-type phenothiazine-thioxanthenes, as phenylbutylpiperidines and also as alkaloids. An example of a piperazine-substituted tricyclic compound of current use in psychotic treatment therapy is fluphenazine [A. F. Gilman et al, *The Pharmacological Basis of Therapeutics*, 7th End., p. 403, MacMillan (1985)].

Tricyclic compounds have been investigated for various CNS uses. For example, Belgian Patent No. 706,262 describes a class of diphenylenemethane amine and amide derivatives mentioned for use as anticonvulsants, as well as for antidepressive, antiinflammatory and analgesic uses, and mentions in particular the compound 2-[fluorene-9-yl)amino]acetamide. U.S. Pat. No. 3,821,249 describes a series of dibenzothiazepin derivatives asserted to possess psychostimulant, antidepressive, analgesic, antitussive, antihistaminic and gastric anti-secretory properties, such series including certain specific 7-[dibenzo(a,d)cycloheptadien-5-yl]aminoheptanoic acid derivatives and certain specific 7-[chlorodibenzo(b,e)thiepin-11-yl]aminoheptanoic acid derivatives.

It has been shown that the sensitivity of central neurons to hypoxia and ischemia can be reduced by either blockage of synaptic transmission or by the specific antagonism of postsynaptic glutamate receptors [see S. M. Rothman et al, *Annals of Neurology*, 19(2), 105–111 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

It is known that compounds of various structures, such aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)piperidinyl]ethanol, which are known anti-ischemic agents, have been found to be non-competitive NMDA receptor antagonist [C. Carter et al, *J. Pharm Exp. Ther.*, 247(3), 1222–1232 (1988)].

Other families of bridged bicyclic amine compounds have been investigated for CNS-related purposes. For example, certain primary and secondary benzobicyclo-[2.2.2]octeneamine compounds have been studied as uptake inhibitors of central catecholamines [R. M. Bartholow et al, *J. Pharm. Exp. Ther.*, 202(3), 532–543 (1977)]. Also, U.S. Pat. No. 4,801,753 describes a family of 4-aminobenzo(b)bicyclo[3.3.1]nonene derivatives an antidepressant agents.

DESCRIPTION OF THE INVENTION

Treatment of CNS disorders and diseases such as psychotic disorders, convulsions, cerebral ischemia and dystonic disorders, may be accomplished by administration of a therapeutically-effective amount of a compound of Formula I:

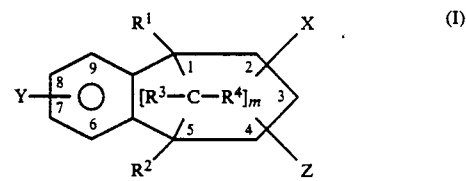

wherein X is a single group selected from

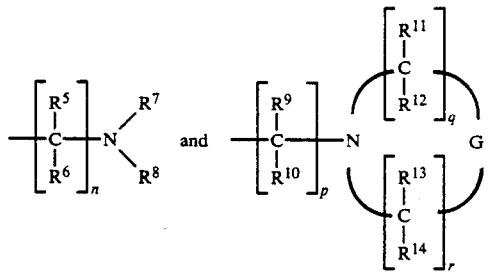

wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkoxycarbonyl, alkenyl and alkynyl; wherein $R^3$ and $R^4$ may be taken together to form oxo; aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^{11}$ and $R^{12}$ may be taken together to form oxo; wherein $R^{13}$ and $R^{14}$ may be taken together to form oxo; wherein each of $R^7$ and $R^8$ is independently selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkylsulfinyl, alkylsulfonyl, arylsulfinyl and arylsulfonyl; wherein G is selected from

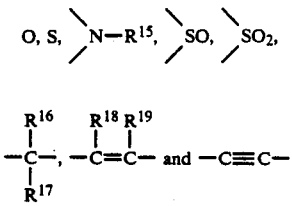

wherein each of $R^{15}$, $R^{18}$ and $R^{19}$ is independently selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkoxycarbonyl and alkanoyl; wherein $R^{16}$ and $R^{17}$ may be taken together to form oxo;

wherein m is one or two; wherein n or p is a number selected from zero through four, inclusive, wherein each of q and r is a number independently selected from one through five, inclusive, with the proviso that sum of q and r is a number from three through ten, inclusive; with the further proviso that X must be attached at one position selected from $R^3$, $R^4$, ring-position two, ring-position three and ring-position four; or the pharmaceutically-acceptable salts thereof.

A preferred class of compounds consists of those compounds within Formula I wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, carboxy, carboxyalkyl, alkanoyl, alkoxycarbonyl, alkenyl and alkynyl; wherein $R^3$ and $R^4$ may be taken together to form oxo; wherein each of $R^5$, $R^6$, $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl and carboxy; wherein each of $R^7$ and $R^8$ is independently selected from hydrido, alkyl, cycloalkyl, hydroxyalkyl, fluoroalkyl, cycloalkylalkyl, alkoxyalkyl, aralkyl, aryl, alkenylalkyl, and alkynylalkyl; wherein G is selected from

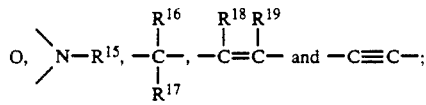

wherein each of $R^{15}$, $R^{19}$ is independently selected from hydrido, alkyl, cycloalkyl, cycloalkylalkyl, aryl, aralkyl, heteroaryl, alkoxyalkyl, hydroxyalkyl, alkanoyl, aralkanoyl and aroyl; wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, fluoroalkyl, hydroxyalkyl, fluoro, alkoxycarbonyl and alkanoyl; wherein m is one or two; wherein n or p is a number selected from zero through four, inclusive; wherein each of q and r is a number independently selected from one through five, inclusive, with the proviso that sum of q and r is a number from three through six, inclusive; with the further proviso that X must be attached at one position selected from $R^3$, $R^4$, ring-position two, ring-position three and ring-position four; or the pharmaceutically-acceptable salts thereof.

A first sub-set of preferred compounds consists of non-cyclic amine compounds within Formula I wherein X is

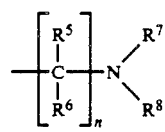

wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo; wherein each of $R^5$ and $R^6$ is independently selected from hydrido, alkyl, cycloalkyl, hydroxyalkyl, fluoroalkyl, cycloalkylalkyl, alkoxyalkyl, phenalkyl and phenyl; wherein each of $R^7$ and $R^8$ is independently selected from hydrido, alkyl, cycloalkyl, hydroxyalkyl, fluoroalkyl, cycloalkylalkyl, alkoxyalkyl, phenalkyl, phenyl, alkenylalkyl and alkynylalkyl; wherein m is one or two; wherein n is a number selected from zero through four, inclusive, with the proviso that X must be attached at one position selected from $R^3$, $R^4$, ring-position two, ring-position three and ring-position four; or the pharmaceutically-acceptable salts thereof.

A more preferred class of compounds within this first sub-set of non-cyclic amine compounds consists of those compounds of Formula I wherein each of $R^1$, $R^2$, $R^3$, $R^4$, Y and Z is independently selected from hydrido, alkyl, alkoxy, halo and haloalkyl; wherein each of $R^5$ and $R^6$ is independently selected from hydrido, alkyl and phenyl; wherein each of $R^7$ and $R^8$ is independently selected from hydrido, alkyl, phenalkyl, phenyl and alkenylalkyl; wherein m is one or two; wherein n is a number selected from zero through two, inclusive; with the proviso that X must be attached at ring-position two; or the pharmaceutically-acceptable salts thereof.

A second sub-set of preferred compounds of Formula I consists of those cyclic amine compounds of Formula II

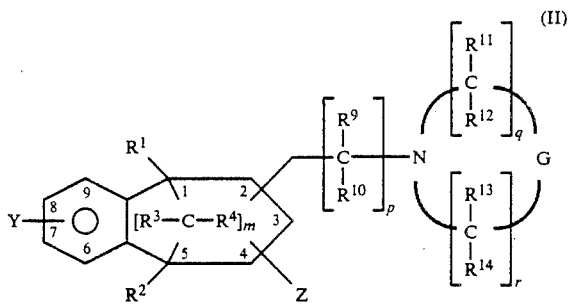

wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo; wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, phenalkyl and phenyl; wherein G within the nitrogen-containing cyclohetero moiety of Formula II is selected from

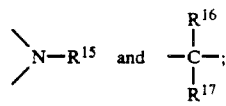

wherein $R^{15}$ is selected from hydrido, alkyl, cycloalkyl, cycloalkylalkyl, phenyl, phenalkyl, alkoxyalkyl and hydroxyalkyl; wherein each of $R^{16}$ and $R^{17}$ is independently selected from hydrido, hydroxy, alkyl, phenalkyl, phenyl, alkoxy, fluoroalkyl and fluoro; wherein m is one or two; wherein p is a number selected from zero through four, inclusive; wherein each of q and r is a number independently selected from one through three, inclusive, with the proviso that sum of q and r is a number from three through six, inclusive; with the further proviso that said nitrogen-containing cyclohetero moiety must be attached to one position selected from $R^3$, $R^4$, ring-position two, ring-position three and ring-position four; or the pharmaceutically-acceptable salts thereof.

With the cyclic amine class of preferred compounds of Formula II is a more preferred sub-class of piperidine compounds of Formula III:

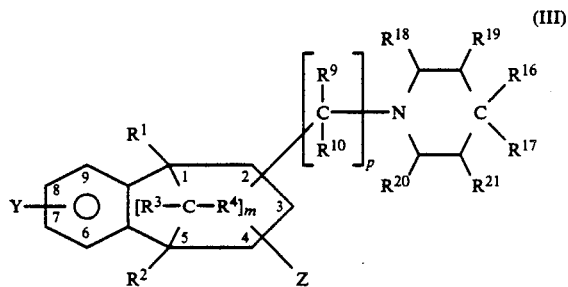

wherein each of $R^1$, $R^2$, $R^3R^4$, Y and Z is independently selected from hydrido, hydroxy, alkyl, benzyl, phenyl, alkoxy, halo and haloalkyl; wherein each of $R^9$ and $R^{10}$ is independently selected from hydrido, alkyl, fluoroalkyl, benzyl and phenyl; wherein each of $R^{16}$ through $R^{21}$ is independently selected from hydrido, hydroxy, alkyl, benzyl, phenyl, alkoxy, fluoroalkyl and fluoro; wherein m is one or two; wherein p is zero or one; or a pharmaceutically-acceptable salt thereof.

An even more preferred class of piperidine compounds of Formula III are those compounds wherein each of $R^1$, $R^2$, $R^3$, $R^4$, Y and Z is independently selected from hydrido, alkyl, halo and haloalkyl; wherein each $R^{16}$ through $R^{21}$ is independently selected from hydrido, alkyl, benzyl and phenyl; wherein m is two; wherein p is zero; or a pharmaceutically-acceptable salt thereof.

Especially preferred compounds within Formula III are the compounds 1-(2-benzobicyclo[3.2.2]nonenyl)-piperidine; exo-1-(2-benzobicyclo[3.2.2]nonenyl)piperidine; and endo-1-(2-benzobicyclo[3.2.2]nonenyl)-piperidine.

Another more preferred sub-class of preferred cyclic amines within Formula II consists of those piperazine compounds of Formula IV

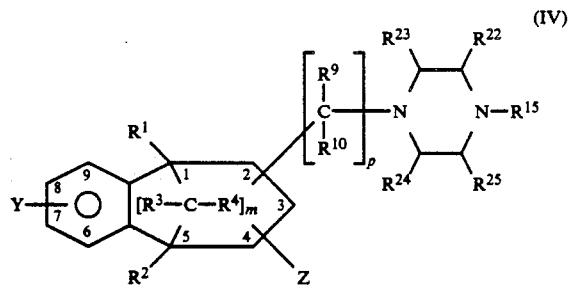

wherein each of $R^1$, $R^2$, $R^3$, $R^4$, Y and Z is independently selected from hydrido, hydroxy, alkyl, benzyl, phenyl, alkoxy, halo and haloalky; wherein each of $R^9$ and $R^{10}$ is independently selected from hydrido, alkyl, fluoroalkyl, benzyl and phenyl; wherein $R^{15}$ is selected from hydrido, alkyl, phenyl, benzyl, alkoxyalkyl and hydroxyalkyl; wherein each of $R^{22}$ through $R^{25}$ is independently selected from hydrido, alkyl, benzyl, phenyl, alkoxy and fluoroalkyl; wherein m is one or two; wherein p is zero or one; or the pharmaceutically-acceptable salts thereof.

An even more preferred group of piperazine compounds within Formula IV consists of those compounds wherein each of $R^1$, $R^2$, $R^3$, $R^4$, Y and Z is independently selected from hydrido, alkyl, halo and haloalkyl; wherein $R^{15}$ is selected from hydrido, alkyl, phenyl, benzyl and hydroxyalkyl; wherein each of $R^{22}$ through $R^{25}$ is independently selected from hydrido, alkyl, benzyl and phenyl; wherein m is two; wherein p is zero; or a pharmaceutically-acceptable salt thereof.

Especially-preferred piperazine compounds of Formula IV are the compounds 1-(2-benzobicyclo-[3.2.2]nonenyl)-4-methylpiperazine.

The phrase "therapeutically-effective amount" means that amount of one or more compounds of Formula I–IV which provides a therapeutic benefit in treatment or management of a CNS disorder or a neurodegenerative disease. A "therapeutically-effective amount" of a compound of Formula I would be an amount of the compound which is effective to treat a psychotic disorder, a convulsive disorder or a dystonic disorder. In cases of treatment of a neurodegenerative disease, the amount of a "therapeutically-effective amount" of a compound of Formula I would be that amount effective to reduce or prevent neurodegeneration arising from or causing CNS disorders such as convulsions and epilepsy.

The term "hydrido" denotes a single hydrogen atom (H) which may be attached, for example, to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to ten carbon atoms, such as cyclopropyl, cyclobutyl, cyclohexyl and cycloheptyl. An example of "cycloalkylalkyl" is cyclohexylmethyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy" embraces linear or branched oxy-containing radicals having an alkyl portion of one to about ten carbon atoms, such as methoxy, ethoxy, isopropoxy and butoxy. An example of "cycloalkyloxy" is cyclohexyloxy. An example of "alkoxyalkyl" is methoxymethyl. An example of "aralkyloxy" is benzyloxy. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals

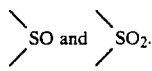

The terms "monoalkylamino" and "dialkylamino" denote amino groups which have been substituted, respectively, with one alkyl radical and with two alkyl radicals. The term "acyl" whether used alone, or within a term such as acyloxy, denotes a radical provided by the residue after removal of hydroxyl from an organic acid, examples of such radical being acetyl and benzoyl.

Within this class of compounds of Formulas I to IV are the tautomeric forms of the described compounds, isomeric forms including diastereoisomers and the pharmaceutically-acceptable salts of such compounds. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxy-ethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. Mixtures of these resulting diastereoisomers may be separated by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

General Synthetic Procedures

Compounds of Formulas I-IV may be prepared in accordance with the following general procedures:

Generic Procedure I

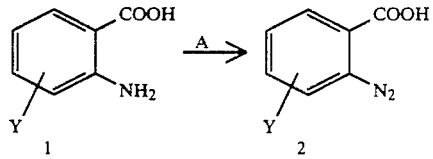

wherein Y is as defined before; wherein A can be a variety of nitrite reagents such as sodium nitrite, isoamyl nitrite or amyl nitrite.

One of the process that can be used to synthesize the products of the invention starts with anthranilates of general structure 1 where Y has the value assigned previously. The anthranilate is treated with the nitrite reagent A in the presence of a catalytic amount of Bronsted acids like hydrochloric acid, trifluoroacetic acid or sulfuric acid to generate the diazonium salt of general structure 2. The reaction is best achieved by mixing the reagents in a solvent like tetrahydrofuran or ether. The temperature of the reaction can vary from about −15° C. to room temperature.

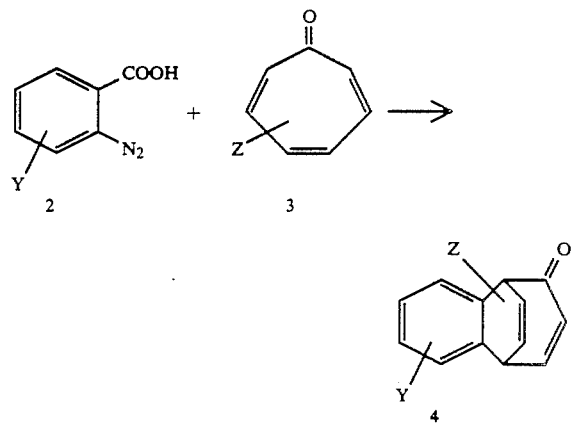

wherein Y and Z are as defined previously.

In the second step of the process, the diazonium salt 2 is transformed into the bicyclic compound 4 by mixing with the ketone 3 where Z has the value assigned previously. The reagents are combined in a solvent such as ether or tetrahydrofuran. The reaction temperature may vary from room temperature to reflux of the reaction mixture.

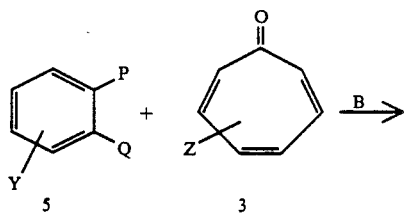

wherein Y and Z are as defined previously; wherein P and Q are halogens selected from fluoro, chloro, bromo or iodo; wherein B is a metal such as magnesium.

Alternately, the bicylic compound 4 can be prepared by combining the ketone 3 with the dihaloaryl 5, where P and Q are halogens selected from fluoro, chloro, bromo, or iodo, and with a metal such as magnesium. The reagents are combined in a solvent such as ether, tetrahydrofuran, or diglyme. The temprature of the reaction may vary from room temperature to reflux of the reaction mixture.

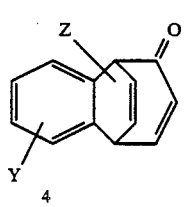

wherein Y and Z are as defined previously.

In the third step of the process, the bicyclic compound 4 is reduced to ketone 6 by reaction with hydrogen in the presence of a variety of catalysts such as palldium on carbon, platinum oxide or other catalysts familiar to those skilled in the art. The catalyst and 4 are combined in a solvent such as ethanol, methanol, or ethyl acetate and the temperature of the reaction can vary from room temperature to about 40° C.

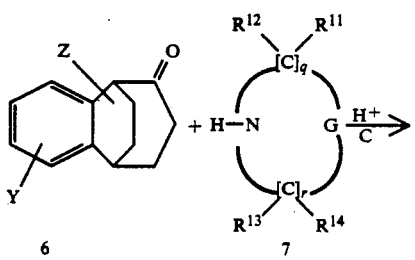

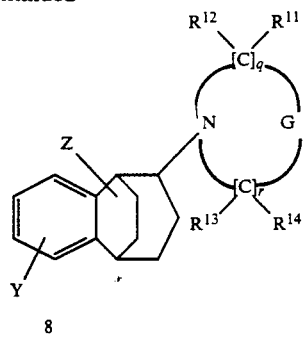

wherein G, Y, Z, q, r, and $R^{11}$ through $R^{14}$ are as defined previously; wherein C is a reducing agent such as sodium cyanoborohydride or sodium borohydride.

In the fourth step of the process, the ketone 6 is converted to the amine 8 by mixing 6 with the amine 7 where G, q, r, and $R^{11}$ through $R^{14}$ are as previously defined. The reagents are mixed in the presence of an acid catalyst such as p-toluenesulfonic acid, trifluoroacetic acid, or acetic acid and with a reducing agent C in a solvent such as ethanol, methanol, or ethyl acetate. The reducing agent C can be a reagent such as sodium cyanoborohydride, sodium borohydride or another reducing agent familiar to those skilled in the art. The temperature of the reaction may vary from room temperature to reflux of the reaction mixture.

Generic Procedure II

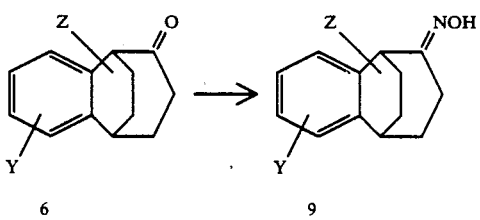

wherein Y and Z are as defined previously.

An alternate process that can be used to synthesize the products of the invention starts with the ketone 6 as prepared by Generic Procedure I where Y and Z are previously described. The ketone 6 is combined with hydroxylamine or its acid addition salts in a solvent or a mixture of solvents such as ethanol, methanol, toluene or water. The temperature of the reaction can vary from room temperature to reflux of the reaction mixture.

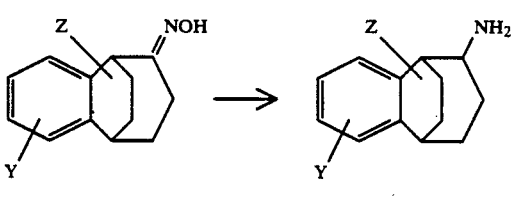

wherein Y and Z are as defined previously.

In the second step of the process, oximes of general structure 9 are converted to amines of general structure 10 by reaction with a reducing agent such as lithium aluminum hydride, sodium borohydride, hydrogen in the presence of a catalyst, or a variety of other reducing systems familiar to those skilled in the art. The reagents are combined in a solvent such as ether, tetrahydrofuran, ethanol, or methanol and the reaction temperature can vary from room temperature to reflux of the reaction mixture.

temperature of the reaction can vary from about $-15°$ C. to room temperature.

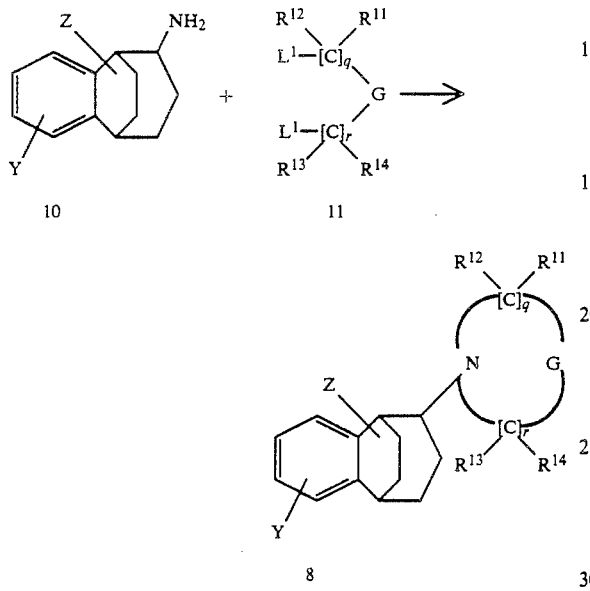

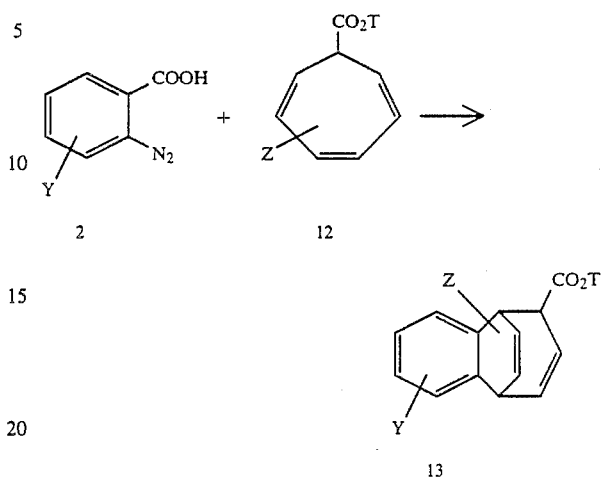

wherein G, Y, Z, q, r, and $R^{11}$ through $R^{14}$ are as defined previously; wherein $L^1$ represents a good leaving group such as chloro, bromo, mesyl, or tosyl.

In the third step of the process, amines of general structure 8 are prepared by combining amines of general structure 10 with compounds of general structure 11 where G q, r, and $R^{11}$ through $R^{14}$ are as defined previously and $L^1$ represents a good leaving group such as chloro, bromo, mesyl or tosyl. The compounds can be combined in a variety of solvents such as toluene, dimethylformamide, acetonitrile or ethanol. The temperature of the reaction can vary from room temperature to reflux of the reaction mixture.

Generic Procedure III

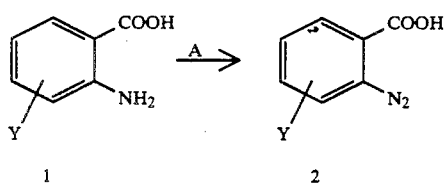

wherein Y is as defined before; wherein A can be a variety of nitrite reagents such as sodium nitrite, isoamyl nitrite or amyl nitrite.

A third process that can be used to synthesize the products of the invention starts with anthranilates of general structure 1 where y has the value assigned previously. The anthranilate is treated with the nitrite reagent A in the presence of a catalytic amount of Bronsted acids like hydrochloric acid, trifluoroacetic acid or sulfuric acid to generate the diazonium salt of general structure 2. The reaction is best achieved by mixing the reagents in a solvent like tetrahydrofuran or ether. The wherein Y and Z are as defined previously; wherein T represents an alkyl or aryl group such as methyl, ethyl, benzyl or phenyl.

In the second step of the process, the diazonium salt 2 is transformed into the bicyclic compound 13 by mixing with the carboxylate ester 12 where Z has the value assigned previously and where T represents an alkyl or aryl group such as methyl, ethyl, benzyl or phenyl. The reagents are combined in a solvent such as ether or tetrahydrofuran. The reaction temperature may vary from room temperature to reflux of the reaction mixture.

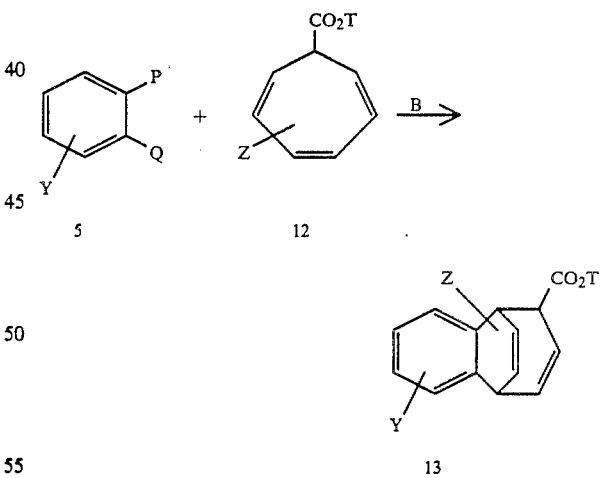

wherein T, Y and Z are as defined previously; wherein P and Q are halogens selected from fluoro, chloro, bromo or iodo; wherein B is a metal such as magnesium.

Alternately, the bicylic compound 13 can be prepared by combining the carboxylate ester 12 with the dihaloaryl 5, where P and Q are halogens selected from fluoro, chloro, bromo, or iodo, and with a metal such as magnesium. The reagents are combined in a solvent such as ether, tetrahydrofuran, or diglyme. The temperature of the reaction may vary from room temperature to reflux of the reaction mixture.

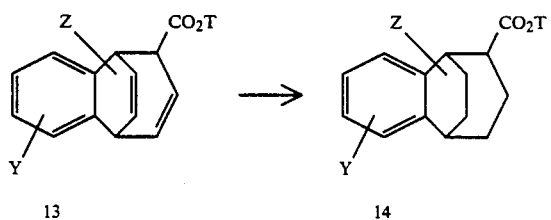

wherein T, Y and Z are as defined previously.

In the third step of the process, the bicyclic compound 13 is reduced to carboxylate ester 14 by reaction with hydrogen in the presence of a variety of catalysts such as palldium- on carbon, platinum oxide or other catalysts familiar to those skilled in the art. The catalyst and 13 are combined in a solvent such as ethanol, methanol, or ethyl acetate and the temperature of the reaction can vary from room temperature to about 40° C.

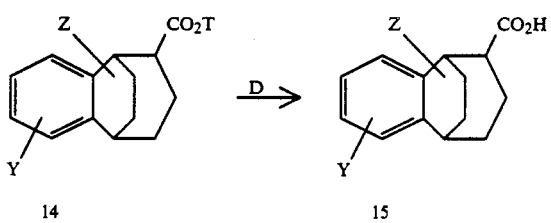

wherein T, Y and Z are as defined before; wherein D is selected from a variety of bases such as sodium hydroxide, lithium hydroxide or potassium hydroxide.

In the fourth step of the process, the ester 14 is hydrolyzed to the acid 15 by mixing the ester with water in the presence of a base such as sodium hydroxide, lithium hydroxide, or potassium hydroxide. The reaction is best achieved by mixing the reagents neat or in a solvent such as ethanol or methanol. The reaction temperature can vary from about room temperature to reflux of the reaction mixture.

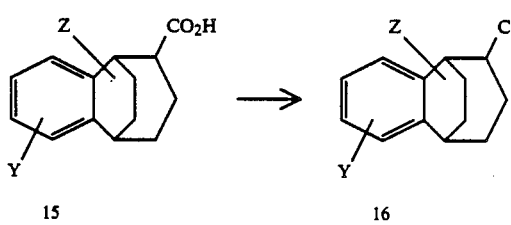

wherein Y and Z are as defined before; wherein $L^2$ represents a good leaving group such as chloro, bromo, or acyl.

In the fifth step of the process, the acid 15 is converted to a compound of general structure 16 where $L^2$ is a good leaving group such as chloro, bromo, or acyl. The conversion can be best achieved by mixing the acid 15 with reagents such as thionyl chloride, phosphorous oxychloride, phosphorous tribromide, or other reagents. This conversion is best achieved by mixing the reagents neat or in an aprotic solvent such as tetrahydrofuran, methylene chloride, or ether. The temperature of the reaction can vary from room temperature to reflux of the reaction mixture.

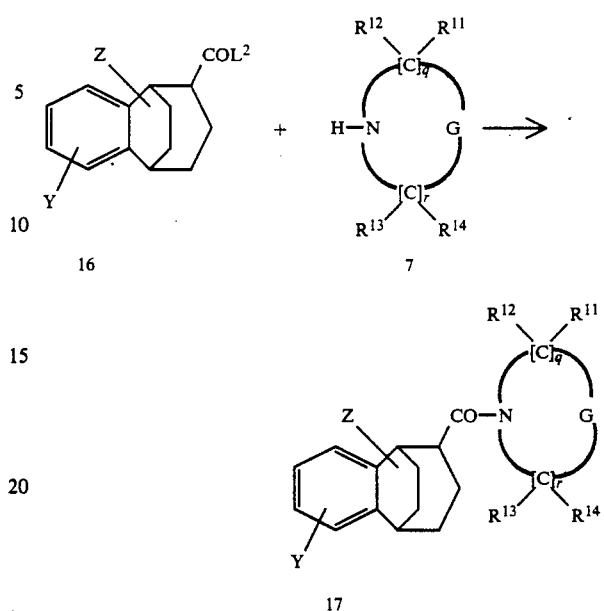

wherein Y, Z, $L^2$, G, q, r, and $R^{11}$ through $R^{14}$ are as previously defined.

In the sixth step of the process, compounds of general structure 16 are converted to amides of general structure 17 by reaction with amines of general structure 7, where G q, r, and $R^{11}$ through $R^{14}$ are as defined before. The conversion is best achieved by mixing the reagents neat or in an aprotic solvent such as tetrahydrofuran, ether, or methylene chloride. The temperature of the reaction can vary from about 0° C. to reflux of the reaction mixture.

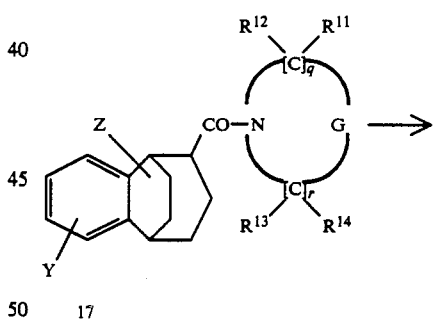

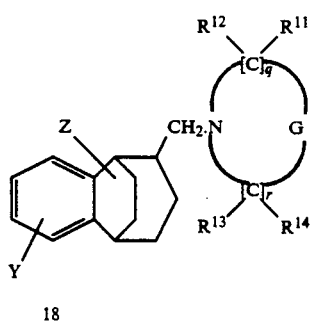

wherein Y, Z, $L^2$, G, q, r, and $R^{11}$ through $R^{14}$ are as previously defined.

In the seventh step of the process, amides of general structure 17 are converted to amines of general structure 18 by employing reducing agents such as lithium aluminum hydride, sodium cyanoborohydride, sodium borohydride, or other reducing agents familiar to those skilled in the art. This reduction can be accomplished in either protic or aprotic solvents, depending on the reducing agent of choice, and at temperatures ranging from room temperature to reflux of the reaction mixture.

The following Examples I-VII are detailed descriptions of the methods of preparation of compounds of Formula I-IV. These detailed preparations fall within the scope of, and serve to exemplify, the above described Generic Procedures which form part of the invention. These Examples I-VII are presented for illustrative purposes only and are not intended as a restriction on the scope of the invention. All parts are by weight unless otherwise indicated. Most of the commercially available starting materials were obtained from Alderich Chemical Company, Milwaukee, Wis.

EXAMPLE I

Benzobicyclo[3.2.2]nonatriene-2-one

Anthranilic acid (10.96 g) was combined with tetrahydrofuran (120 ml) and trifluoroacetic acid (0.25 ml) and cooled to 0° C. Isoamyl nitrite (20 ml) was added to the cold solution and the mixture stirred for 30 minutes at 0° C. and 30 minutes at room temperature. The precipitated material was filtered and washed with cold tetrahydrofuran (200 ml). The wet precipitate was combined with tetrahydrofuran (270 ml) and 2,4,6-cycloheptatrieneone (8.06 g) and the mixture heated to 40° C. for 20 hours. The reaction solvent was removed on a rotary evaporator and the residual material placed on a silica gel column. The reaction product was eluted from the column with 5% ethyl acetate in hexane to provide the intermediate benzobicyclo[3.2.2]nonatriene-2-one as a yellow oil.

EXAMPLE II

Benzobicyclo[3.2.2]nonene-2-one

Benzobicyclo[3.2.2]nonatriene-2-one (4.8 g) was combined with ethanol (25 ml) and a catalytic amount of 10% palladium on carbon. The mixture was hydrogenated at 5 psi for 30 minutes at room temperature. The catalyst was removed by filtration and the ethanol removed on a rotary evaporator. The residue was distilled on a Kugelrohr apparatus (100° C. at 0.05 mm Hg) to provide the product as a colorless oil.

EXAMPLE III

2-Aminobenzobicyclo[3.2.2]nonene

Benzobicyclo[3.2.2]nonene-2-one (4.7 g) was combined with pyridine (50 ml) and methoxyamine hydrochloride (4.69 g) and heated to reflux for 20 hours. The reaction solvent was removed on a rotary evaporator and the residue was partitioned between water (50 ml) and ether (50 ml). The aqueous layer was extracted with ether (2×50 ml) and the combined ether solutions were washed with water (50 ml). The ether solution was dried over magnesium sulfate and concentrated on a rotary evaporator. The residue was combined with tetrahydrofuran (50 ml) and treated dropwise with 1M borane in tetrahydrofuran (30 ml). The solution was heated to reflux for 20 hours, then cooled to room temperature. The solution was poured into 1N hydrochloric acid (100 ml) and the resulting mixture washed with ether (3×50 ml). The combined ether washes were extracted with 6N hydrochloric acid (30 ml) and the combined aqueous solutions were made basic by the addition of concentrated aqueous ammonia. The resulting mixture was extracted with ether (3×70 ml) and the combined ether extracts were dried over magnesium sulfate and concentrated on a rotary evaporator to provide the product as a yellow oil.

EXAMPLE IV exo- and endo-1-(2-Benzobicyclo[3.2.2]nonenyl)piperidine (Compound No. 1)

2-Aminobenzobicyclo[3.2.2]nonene (2.56 g) was combined with potassium carbonate (2 g), 1,5-dibromopentane (2.4 ml), and acetonitrile (75 ml) and the mixture heated to reflux for 24 hours. The mixture was poured into water (100 ml) and the aqueous mixture was extracted with ether (3×75 ml). The combined ether extracts were dried over magnesium sulfate and concentrated on a rotary evaporator. The residue was distilled on a Kugelrohr apparatus (120° C. at 0.06 mm Hg) to provide the product as a light yellow oil. Physical data are reported in Table I.

EXAMPLE V exo-1-(2-Benzobicyclo[3.2.2]nonenyl)piperidine

The mixture of exo- and endo-1-(2-benzobicyclo-]3.2.2[nonenyl)piperidine (2.5 g) was separated using silica gel chromatography with 30% ethyl acetate in hexane as the eluant. The first material to elute was collected and the eluant removed on a rotary evaporator to provide the product as a colorless oil. Physical data are reported in Table I.

EXAMPLE VI endo-1-(2-Benzobicyclo[3.2.2]nonenyl)piperidine (Compound No. 3)

The second material to elute from the column described in Example Procedure V was collected and the eluant removed on a rotary evaporator to provide the product as a colorless oil. Physical data are reported in Table I.

EXAMPLE VII endo- and exo-1-(2-Benzobicyclo[3.2.2]nonenyl)-4-(2-hydroxyethyl)piperazine (Compound No. 4)

Benzobicyclo[3.2.2]nonene-2-one (1 g) was combined with 1-(2-hydroxy-ethyl)piperazine (3 ml) and xylene (10 ml) and heated to reflux for 24 hours. p-Toluenesulfonic acid (100 mg) was added to the reaction solution and heating was continued for 24 hours. The xylene was removed on a rotary evaporator and the residue was combined with ethanol (20 ml) and sodium borohydride (1 g). The solution was heated to reflux for 2 hours and the solvent removed on a rotary evaporator. The residue was suspended between ether (75 ml) and water (50 ml). The layers were separated and the ether layer was washed with water (2×50 ml), then extracted with 3N hydrochloric acid (3×25 ml). The combined acid solutions were made basic by the addition of concentrated aqueous ammonia and the resulting mixture was extracted with methylene chloride (3×25 ml). The combined methylene chloride solutions were dried over magnesium sulfate and the solvent removed on a rotary evaporator. The residue was combined with ether (50 ml) and the solution was treated with a solution of 48% hydrogen bromide (0.81 ml) in 2-propanol (10 ml). The precipitated material was removed by filtration and recrystallized from 2-propanol to provide the product as a white solid. Physical data are reported in Table I.

Table I is a list of 5 specific compounds of most interest within Formula I. The preparation of representative compounds from Table I is described in detail in Example Procedures I-VII, above.

nate was centrifuged at 900×G for 10 minutes at 4° C. The supernatant was collected and centrifuged at 22,000×g for 20 minutes at 4° C. The pellet was resuspended in 10 volumes of 50 mM Tris/HCl buffer (pH 7.4) and centrifuged at 22,000×g for 20 minutes at 4° C. The pellet was resuspended in 5 mM Tris/HCl buffer (pH 7.4) to give a final concentration of 250 mg/ml of the crude material. Incubation tubes were prepared in triplicate and contained 0.1 ml of tissue suspension, 2

TABLE I

| Compound No. | Name | Structure | Method of Preparation | Elemental Analysis | Theor. | Found |
|---|---|---|---|---|---|---|
| 1 | 1-(2-benzobicyclo-[3.2.2.]nonenyl)piperidine | 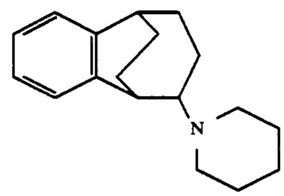 | I-IV | C<br>H<br>N | 84.65<br>9.87<br>5.48 | 84.85<br>9.92<br>5.47 |
| 2 | exo-1-(2-benzobicyclo[3.2.2.]nonenyl)-piperidine.0.03CH$_2$Cl$_2$ | 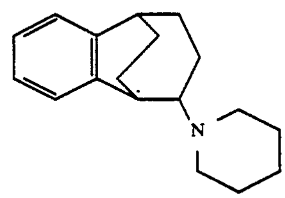 | V | C<br>H<br>N | 83.99<br>9.80<br>5.43 | 84.00<br>9.78<br>5.37 |
| 3 | endo-1-(2-benzobicyclo[3.2.2.]nonenyl)-piperidine.0.1CH$_2$Cl$_2$ | 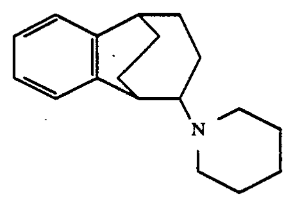 | VI | C<br>H<br>N | 82.82<br>9.67<br>5.34 | 82.84<br>9.77<br>4.93 |
| 4 | 1-(2-benzobicyclo-[3.2.2.]nonenyl)-4-(2-hydroxyethyl)-piperazine.2HCl.0.14H$_2$O | 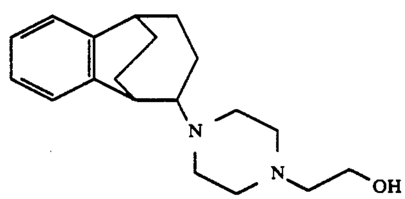 | I, II, VII | C<br>H<br>N | 48.95<br>6.51<br>6.01 | 48.95<br>6.51<br>5.97 |
| 5 | 1-(2-benzobicyclo[3.3.2]-nonenyl)-4-methylpiperazine 3.26HCl.1.17H$_2$O | 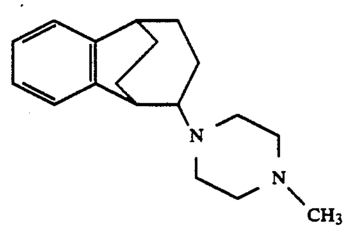 | I-IV | C<br>H<br>N | 52.67<br>7.76<br>6.82 | 52.54<br>7.76<br>7.80 |

BIOLOGICAL EVALUATION

Radioreceptor Assay

Compounds 1-5 were compared against di-o-tolylguanidine (DTG) [E. Weber et al, *Proc. Natl. Acad. Sci.*, 83, 8784-8788, 1986] to determine the relative potency of the compounds interacting with the sigma receptor. To determine the effects of the compounds in a sigma receptor assay, crude membrane preparations were prepared as follows. Brains from male Sprague-Dawley rats were homogenized in 10 volumes (wt/vol) of 0.32M sucrose, using a Polytron grinder. The homogenate nM of [$^3$H]-(+)-1-propyl-3-(3-hydroxyphenyl)piperidine [$^3$H]-3-(+)-PPP, and varying concentrations of the displacing ligand (0.1-1,000 nM) in a final volume of 0.5 ml. After a 1 hr incubation at room temperature, the contents of the test tubes were filtered through GS filter paper which had been presoaked for at least 2 hours in 0.05% polyethyleneimine. The test tubes were rinsed three times with Tris/HCl buffer. Radioactivity on the filters was determined using liquid scintillation spectrometry and inhibition curves were calculated according to the method of Cheng and Prusoff [*Biochem. Pharmacol.,* 22, 3099–3108 (1973)].

TABLE II

| Test Compound | Ki apparent (nM) (units ± SEM) |
|---|---|
| DTG | 47 ± 5 |
| Compound No. 1 | 6 ± 1 |
| Compound No. 2 | 10 ± 2 |
| Compound No. 3 | 150 ± 20 |
| Compound No. 4 | 305 ± 20 |
| Compound No. 5 | 16000 ± 4000 |

Blockade of Agonist-induced Stereotyped Behavior and Ataxia

Compounds of the invention were evaluated for their ability to block the effects of N-allylnormetazocine on the induction of stereotyped behavior and ataxia. To test for antagonism, drugs are administered at varying times before i.p. administration of 15 mg/kg of N-allylnormetazocine. Behavioral and ataxia ratings are taken at 2.5 minutes, 5 minutes, and every 5 minutes thereafter until the animal returns to control behavior. The rating scale for stereotyped behavior is: (0) inactive or in-place non-repetitive activity; (1) sniffing, grooming, or rearing; (2) undirected head movements, reciprocal forepaw treading or a greater frequency of sniffing than in (1); (3) appearance of circling, weaving or backward walking; (4) gagging or continuous circling, weaving or backward walking; and (5) dyskinetic extension or flexation of head, neck and limbs, or rapid and continuous weaving greater than (4). The rating scale for ataxia is: (0) inactive or coordinated movements; (1) awkward or jerky movements or loss of balance while rearing; (2) stumbles or awkward position; (3) falling or leaning against cage; (4) supports weight on stomach or haunches; and (5) unable to move except for twitching movements. The lowest dose of the test compound which is capable of blocking the stereotyped behavior and ataxia induced by N-allylnormetazocine was determined. For example, at a dose of 1 mg/kg i.p., Compound No. 1 fully blocked N-allylnormetazocine-induced stereotyped behavior.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liqiud. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3,000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

For therapeutic purposes, the compounds of this invention are ordinarily combined wit one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

Although this invention has been described with respect to specific embodiments, the details of these embodiments are not to be construed as limitations. Various equivalents, changes and modifications may be made without departing from the spirit and scope of this

What is claimed is:
1. A compound of the formula

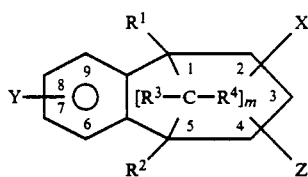

wherein X is

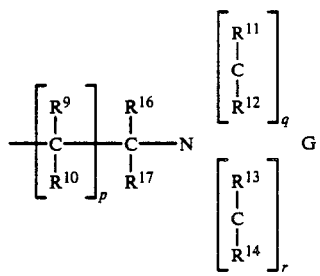

wherein each of R¹, R², R³, R⁴, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkoxycarbonyl, alkenyl and alkynyl; wherein R³ and R⁴ may be taken together to form oxo;
wherein each of R⁹, R¹⁰, R¹¹, R¹², R¹³ and R¹⁴ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein R¹¹ and R¹² may be taken together to form oxo; wherein R¹³ and R¹⁴ may be taken together to form oxo;
wherein G is selected from

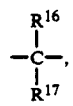

wherein each of R¹⁶ and R¹⁷ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkoxycarbonyl and alkanoyl; wherein R¹⁶ and R¹⁷ may be taken together to form oxo;
wherein m is one or two; wherein p is a number selected from zero through four, inclusive, wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

2. Compound of claim 1 wherein each of R¹, R², R³, R⁴, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, carboxy, carboxyalkyl, alkanoyl, alkoxycarbonyl, alkenyl and alkynyl; wherein R³ and R⁴ may be taken together to form oxo;
wherein each of R⁹, R¹⁰, R¹¹, R¹², R¹³ and R¹⁴ is independently selected from hydrido, alkyl, cycloalkyl, hydroxyalkyl, fluoroalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl and carboxy;
wherein G is selected from

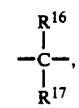

wherein each of R¹⁶ and R¹⁷ is independently selected from hydrido, hydroxy, alkyl, cycloalkyl, cycloalkylalkyl, aralkyl, aryl, alkoxy, aralkoxy, aryloxy, alkoxyalkyl, fluoroalkyl, hydroxyalkyl, fluoro, alkoxycarbonyl and alkanoyl;
wherein m is one or two; wherein p is a number selected from zero through four, inclusive; wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

3. Compound of claim 2 of the formula

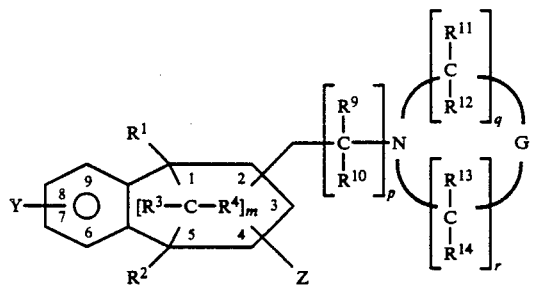

wherein each of R¹, R², R³, R⁴, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein R³ and R⁴ may be taken together to form oxo;
wherein each of R⁹, R¹⁰, R¹¹, R¹², R¹³ and R¹⁴ is independently selected from hydrido, alkyl, cycloalkyl, hydroxyalkyl, fluoroalkyl, cycloalkylalkyl, alkoxyalkyl, phenalkyl and phenyl;
wherein G within the nitrogen-containing cyclohetero moiety is selected from

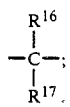

wherein each of $R^{16}$ and $R^{17}$ is independently selected from hydrido, hydroxy, alkyl, phenalkyl, phenyl, alkoxy, fluoroalkyl and fluoro;

wherein m is one or two; wherein p is a number selected from zero through four, inclusive; wherein each of q and r is a number independently selected from one through three, inclusive, with the proviso that sum of q and r is a number from three through six, inclusive; with the further proviso that said nitrogen-containing cyclohetero moiety must be attached at a position selected from ring-position two, ring-position three and ring-position four; or a pharmaceutically-acceptable salt thereof.

4. Compound of claim 3 of the formula

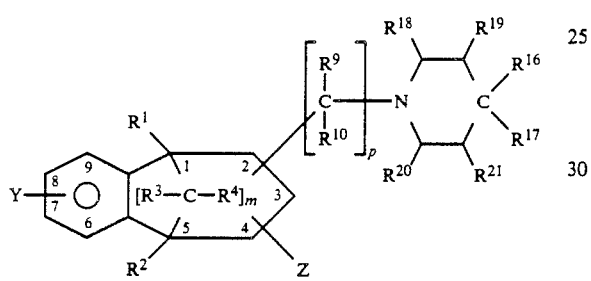

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^9$ and $R^{10}$ is independently selected from hydrido, alkyl, fluoroalkyl, benzyl and phenyl;

wherein each of $R^{16}$ through $R^{21}$ is independently selected from hydrido, hydroxy, alkyl, benzyl, phenyl, alkoxy, fluoroalkyl and fluoro;

wherein X is attached at a position selected from ring-position two, ring-position three and ring-position four;

wherein m is one or two; wherein p is zero or one; or a pharmaceutically-acceptable salt thereof.

5. Compound of claim 4 wherein each of $R^1$, $R^2$, $R^3$, $R^4$, Y and Z is independently selected from hydrido, alkyl, halo and haloalkyl; wherein each $R^{16}$ through $R^{21}$ is independently selected from hydrido, alkyl, benzyl and phenyl; wherein m is two; wherein p is zero; or a pharmaceutically-acceptable salt thereof.

6. Compound of claim 5 selected from 1-(2-benzobicyclo[3.2.2]nonenyl)piperidine; exo-1-(2-benzobicyclo[3.2.2]nonenyl)piperidine; and endo-1-(2-benzobicyclo[3.2.2]nonenyl)piperidine; or a pharmaceutically-acceptable salt thereof.

7. A pharmaceutical composition comprising a therapeutically-effective amount of an active compound for treating or preventing a CNS-related disorder and a pharmaceutically-acceptable carrier or diluent, said active compound selected from a family of compounds of the formula

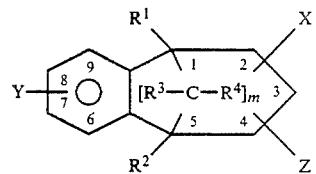

wherein X is

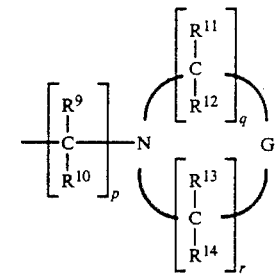

wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkoxycarbonyl, alkenyl and alkynyl; wherein $R^3$ and $R^4$ may be taken together to form oxo; wherein each of $R^9$, $R^{10}$, $R^{11}$, $R^{12}$, $R^{13}$ and $R^{14}$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^{11}$ and $R^{12}$ may be taken together to form oxo; wherein $R^{13}$ and $R^{14}$ may be taken together to form oxo;

wherein G is selected from

wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkoxycarbonyl and alkanoyl; wherein $R^{16}$ and $R^{17}$ may be taken together to form oxo;

wherein m is one or two; wherein p is a number selected from zero through four, inclusive, wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

8. The composition of claim 7 wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, carboxy, carboxyalkyl, alkanoyl, alkoxycarbonyl, alkenyl and alkynyl; wherein $R^3$ and $R^4$ may be taken together to form oxo;

wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl and carboxy;

wherein G is selected from

wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, fluoroalkyl, hydroxyalkyl, fluoro, alkoxycarbonyl and alkanoyl;

wherein m is one or two; wherein p is a number selected from zero through four, inclusive; wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

9. The composition of claim 8 wherein said active compound is of the formula

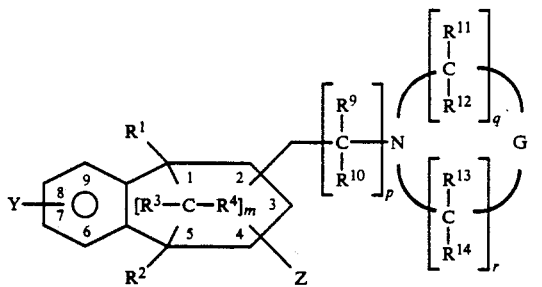

wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo;

wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, phenalkyl and phenyl;

wherein G within the nitrogen-containing cyclohetero moiety is selected from

wherein each of $R^{16}$ and $R^{17}$ is independently selected from hydrido, hydroxy, alkyl, phenalkyl, phenyl, alkoxy, fluoroalkyl and fluoro;

wherein m is one or two; wherein p is a number selected from zero through four, inclusive; wherein each of q and r is a number independently selected from one through three, inclusive, with the proviso that sum of q and r is a number from three through six, inclusive; with the further proviso that said nitrogen-containing cyclohetero moiety must be attached at a position selected from ring-position two, ring-position three and ring-position four; or a pharmaceutically-acceptable salt thereof.

10. The composition of claim 9 wherein said active compound is of the formula

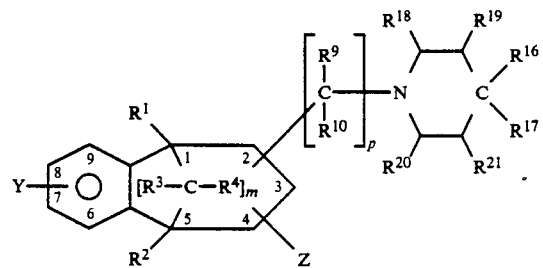

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^9$ and $R^{10}$ is independently selected from hydrido, alkyl, fluoroalkyl, benzyl and phenyl;

wherein each of $R^{16}$ through $R^{21}$ is independently selected from hydrido, hydroxy, alkyl, benzyl, phenyl, alkoxy, fluoroalkyl and fluoro;

wherein X is attached at a position selected from ring-position two, ring-position three and ring-position four;

wherein m is one or two; wherein p is zero or one; or a pharmaceutically-acceptable salt thereof.

11. The composition of claim 10 wherein each of $R^1$, $R^2$, $R^3$, $R^4$, Y and Z is independently selected from hydrido, alkyl, halo and haloalkyl; wherein each $R^{16}$ through $R^{21}$ is independently selected from hydrido, alkyl, benzyl and phenyl; wherein m is two; wherein p is zero; or a pharmaceutically-acceptable salt thereof.

12. The composition of claim 11 wherein said active compound is selected from 1-(2-benzobicyclo-[3.2.2]nonenyl)piperidine; exo-1-(2-benzobicyclo-[3.2.2]nonenyl)piperidine; and endo-1-(2-benzobicyclo[3.2.2]nonenyl)piperidine; or a pharmaceutically-acceptable salt thereof.

13. A method for treating a patient afflicted with or susceptible to a CNS-related disorder, which method comprises administering to the patient a therapeutically-effective amount of a compound of the formula

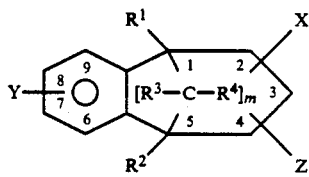

wherein X is

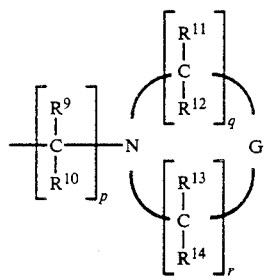

wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkoxycarbonyl, alkenyl and alkynyl; wherein $R^3$ and $R^4$ may be taken together to form oxo;

wherein each of $R^9$, $R^{10}$, $R^{11}$, $R^{12}$, $R^{13}$ and $R^{14}$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^{11}$ and $R^{12}$ may be taken together to form oxo; wherein $R^{13}$ and $R^{14}$ may be taken together to form oxo;

wherein G is selected from

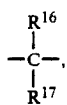

wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkoxycarbonyl and alkanoyl; wherein $R^{16}$ and $R^{17}$ may be taken together for form oxo;

wherein m is one or two; wherein p is a number selected from zero through four, inclusive, wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

14. The method of claim 13 wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, carboxy, carboxyalkyl, alkanoyl, alkoxycarbonyl, alkenyl and alkynyl; wherein $R^3$ and $R^4$ may be taken together to form oxo;

wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl and carboxy;

wherein G is selected from

wherein each of $R^{16}$ and $R^{17}$ is independently selected from hydrido, hydroxy, alkyl, cycloalkyl, cycloalkylalkyl, aralkyl, aryl, alkoxy, aralkoxy, aryloxy, alkoxyalkyl, fluoroalkyl, hydroxyalkyl, fluoro, alkoxycarbonyl and alkanoyl;

wherein m is one or two; wherein p is a number selected from zero through four, inclusive; wherein each of q and r is a number independently selected from one through five, inclusive, with the proviso that sum of q and r is a number from three through six, inclusive; with the further proviso that X must be attached at a position selected from ring-position two, ring-position three and ring-position four; or a pharmaceutically-acceptable salt thereof.

15. The method of claim 14 wherein said compound is of the formula

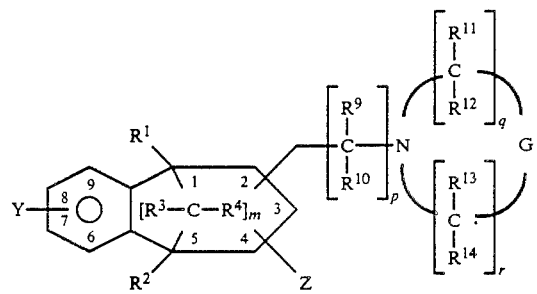

wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo;

wherein each of $R^9$, $R^{10}$, $R^{11}$, $R^{12}$, $R^{13}$ and $R^{14}$ is independently selected from hydrido, alkyl, cycloalkyl, hydroxyalkyl, fluoroalkyl, cycloalkylalkyl, alkoxyalkyl, phenalkyl and phenyl;

wherein G within the nitrogen-containing cyclohetero moiety is selected from

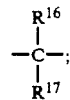

wherein each of $R^{16}$ and $R^{17}$ is independently selected from hydrido, hydroxy, alkyl, phenalkyl, phenyl, alkoxy, fluoroalkyl and fluoro;

wherein m is one or two; wherein p is a number selected from zero through four, inclusive; wherein each of q and r is a number independently selected from one through three, inclusive, with the proviso that sum of q and r is a number from three through six, inclusive; with the further proviso that nitrogen-containing cyclohetero moiety must be attached at a position selected from ring-position two, ring-position three and ring-position four;

or a pharmaceutically-acceptable salt thereof.

16. The method of claim 15 wherein said compound is of the formula

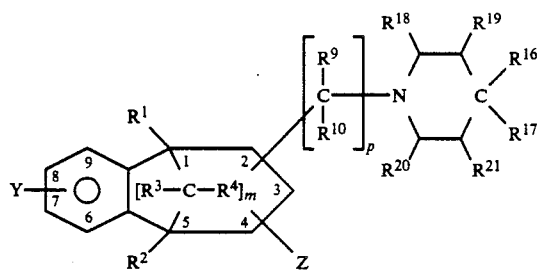

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^9$ and $R^{10}$ is independently selected from hydrido, alkyl, fluoroalkyl, benzyl and phenyl;

wherein each of $R^{16}$ through $R^{21}$ is independently selected from hydrido, hydroxy, alkyl, benzyl, phenyl, alkoxy, fluoroalkyl and fluoro;

wherein X is attached at a position selected from ring-position two, ring-position three and ring-position four;

wherein m is one or two; wherein p is zero or one; or a pharmaceutically-acceptable salt thereof.

17. The method of claim 16 wherein each of $R^1$, $R^2$, $R^3$, $R^4$, Y and Z is independently selected from hydrido, alkyl, halo and haloalkyl; wherein each $R^{16}$ through $R^{21}$ is independently selected from hydrido, alkyl, benzyl and phenyl; wherein m is two; wherein p is zero; or a pharmaceutically-acceptable salt thereof.

18. The method of claim 17 wherein said compound is selected from 1-(2-benzobicyclo[3.2.2]nonenyl)piperidine; exo-1-(2-benzobicyclo[3.2.2]nonenyl)piperidine; and endo-1-(2-benzobicyclo[3.2.2]nonenyl)piperidine; or a pharmaceutically-acceptable salt thereof.

19. The method of claim 13 wherein said CNS-related disorder is cerebral ischemia.

20. The method of claim 13 wherein said CNS-related disorder is a psychotic disorder.

21. The method of claim 13 wherein said CNS-related disorder is a convulsive disorder.

22. The method of claim 13 wherein said CNS-related disorder is dystonia.

* * * * *